(12) United States Patent
Netsner et al.

(10) Patent No.: US 9,597,239 B2
(45) Date of Patent: Mar. 21, 2017

(54) ELONGATED STRIP-LIKE FILM BANDAGE

(75) Inventors: Bengt Netsner, Lindome (SE); Camilla Johansson, Lerum (SE)

(73) Assignee: Mönlycke Health Care AB, Göteborg (SE)

(*) Notice: Subject to any disclaimer, the term of this patent is extended or adjusted under 35 U.S.C. 154(b) by 1060 days.

(21) Appl. No.: 12/522,984

(22) PCT Filed: Feb. 1, 2008

(86) PCT No.: PCT/SE2008/050130
§ 371 (c)(1),
(2), (4) Date: Aug. 19, 2009

(87) PCT Pub. No.: WO2008/097182
PCT Pub. Date: Aug. 14, 2008

(65) Prior Publication Data
US 2010/0094191 A1    Apr. 15, 2010

(30) Foreign Application Priority Data
Feb. 6, 2007  (SE) ...................... 0700292

(51) Int. Cl.
*A61F 15/00*   (2006.01)

(52) U.S. Cl.
CPC .................. *A61F 15/002* (2013.01)

(58) Field of Classification Search
CPC ............. Y10S 206/82; Y10S 602/90; A61F 13/15747; A61F 15/001; A61F 15/002; A61F 13/041; A61F 13/0276; A61F 13/00076; A61F 13/0269; A61F 2013/00897; B65H 45/1015; A47K 2010/428; A47K 10/42; B65D 85/62
(Continued)

(56) References Cited

U.S. PATENT DOCUMENTS 1,208,701 A * 12/1916 Trenner ........................ 206/440
2,292,995 A *  8/1942 Greenwoll ..................... 602/42
(Continued)

FOREIGN PATENT DOCUMENTS

DE      38 21 698       1/1990
DE      3821698 A1      1/1990
(Continued)

OTHER PUBLICATIONS

International Search Report dated Apr. 9, 2008, from corresponding PCT application.
(Continued)

*Primary Examiner* — Ophelia A Hawthorne
*Assistant Examiner* — Caitlin Carreiro
(74) *Attorney, Agent, or Firm* — Ballard Spahr LLP

(57) ABSTRACT

An elongated, strip-like film bandage, includes a plastics film (1), which on its one side is coated with a skin-friendly adhesive (2), a protective layer (3) detachably fixed to the adhesive coating, and a stiffening layer (4), which is detachably fixed to the plastics film on the opposite side to the adhesive coating. The bandage is bellows-folded into a stack such that the bandage is divided into a number of parts (6-15) stacked one on top of the other, and three such parts of the bandage, which are mutually adjacent, are connected to one another on two opposite sides of the stack.

12 Claims, 3 Drawing Sheets

(58) Field of Classification Search
USPC ........ 602/41–59, 904; 424/443–449; 221/25, 221/73; 206/411, 441, 601
See application file for complete search history.

(56) References Cited

U.S. PATENT DOCUMENTS

| | | | | |
|---|---|---|---|---|
| 2,587,928 | A | * | 3/1952 | Tuck et al. .................... 221/25 |
| 4,759,652 | A | | 7/1988 | Ulrich |
| 4,837,062 | A | | 6/1989 | Dunshee et al. |
| 4,993,586 | A | | 2/1991 | Taulbee et al. |
| 5,358,140 | A | * | 10/1994 | Pellegrino .................... 221/25 |
| 5,891,078 | A | * | 4/1999 | Turngren et al. .............. 602/58 |
| 6,096,942 | A | * | 8/2000 | Hack ............................ 602/41 |
| 6,849,775 | B2 | * | 2/2005 | Klein ........................... 602/41 |

FOREIGN PATENT DOCUMENTS

| | | |
|---|---|---|
| EP | 0541251 | 5/1993 |
| EP | 0870488 | 10/1998 |
| EP | 1 103 241 | 5/2001 |
| JP | S58-180152 | 10/1983 |
| JP | S60-032917 | 3/1985 |
| JP | H05-208032 | 8/1993 |
| JP | S30-015282 | 8/1995 |
| JP | H08-507417 | 9/1996 |
| JP | H10-263006 | 10/1998 |
| JP | 2001-505462 | 4/2001 |
| JP | H07-040744 | 2/2007 |
| WO | WO 94/21207 | 9/1994 |
| WO | WO 98/24393 | 6/1998 |

OTHER PUBLICATIONS

Written Opinion issued on Apr. 9, 2008 for Intl. App. No. PCT/SE2008/050130, filed on Feb. 1, 2008.
International Preliminary Report on Patentability issued on Aug. 11, 2009 for Intl. App. No. PCT/SE2008/050130, filed on Feb. 1, 2008.
Response to Communication filed on May 11, 2012 for EP Pat. App. No. 08712770.0, national phase of Intl. App. No. PCT/SE2008/050130, filed on Feb. 1, 2008.
Communication from Examining Division issued on Jan. 12, 2012 for EP Pat. App. No. 08712770.0, national phase of Intl. App. No. PCT/SE2008/050130, filed on Feb. 1, 2008.
Preliminary Amendment/Response to Supplementary European Search Report filed on Nov. 15, 2011 for EP Pat. App. No. 08712770.0, national phase of Intl. App. No. PCT/5E2008/050130, filed on Feb. 1, 2008.
Supplementary European Search Report and Opinion issued on Apr. 29, 2011 for EP Pat. App. No. 08712770.0, national phase of Intl. App. No. PCT/5E2008/050130, filed on Feb. 1, 2008.
English translation of communication from the Japanese Patent Office issued on Jul. 3, 2012 for JP Pat. App. No. 2009-549046, national phase of Intl. App. No. PCT/SE2008/050130, filed on Feb. 1, 2008 (pp. 1-5).
Communication from the Japanese Patent Office issued on Jul. 3, 2012 for JP Pat. App. No. 2009-549046, national phase of Intl. App. No. PCT/SE2008/050130, filed on Feb. 1, 2008 (pp. 1-5).

* cited by examiner

ELONGATED STRIP-LIKE FILM BANDAGE

TECHNICAL FIELD

The present invention relates to an elongated, strip-like film bandage, comprising a plastic film, which on its one side is coated with a skin-friendly adhesive, a protective layer detachably fixed to the adhesive coating, and a stiffening layer, which is detachably fixed to the plastic film on the opposite side to the adhesive coating.

BACKGROUND ART

Elongated, strip-like film bandages are traditionally supplied rolled together into a roll. Such bandages are used in parts and the user himself judges how large a part of the bandage is required in each instance and, based on such a judgement, cuts off a suitable length of bandage. Even though the handling of such traditional, elongated strip-like film bandages generally works well, film bandages of this kind do have certain drawbacks in terms of their use. For example, it is in many cases difficult to judge how much of the roll to unwind in order to obtain the desired length of the part which is to be cut off. Since it is time-consuming and sometimes difficult to wind back an unwound part of the roll, an over-unwinding of the roll often leads to the unwound part being cut off from the roll and this cut-off part, in turn, being cut such that a part of suitable length is obtained. The part of unwanted length which is cut off from the first cut-off part is discarded. The roll shape of traditional elongated, strip-like film bandages therefore contributes to the creation of unnecessary material wastage. Furthermore, roll-shaped film bandages must be packed in such a way that the risk of the roll automatically curling up when the user pulls on one end of the bandage is eliminated, which complicates the packaging for the bandage and also contributes to the time wasted in rolling back unwound parts. A further cause of unnecessary material wastage is that at the end of traditional elongated, strip-like film bandages, i.e. when the greatest part of the roll is unwound, a lifting of the free end of the remaining length of the traditional elongated, strip-like film results in the entire length of remaining film bandage being lifted out of its packaging, which leads to material wastage unless the remaining length of the film bandage were to coincide with the length of bandage required. It is additionally pointed out that the central part of a rolled-up traditional elongated, strip-like film is often difficult or impossible to use owing to the fact that this part tries to maintain its curved, rolled-up shape. This can, of course, be combated by winding the bandage around an annular core, so that the radius of curvature for the central part of the roll is relatively large, but such a measure adds to the material costs and makes the bandage more bulky. It is pointed out that the tendency of the traditional elongated, strip-like film bandage to resume a rolled-up shape can make it more difficult to cut off unwound parts, at least at the end of the bandage, since the extracted part of the bandage must be kept taut during the cutting.

The object of the present invention is to provide an elongated, strip-like film bandage without the abovementioned drawbacks, which is easy to divide into a number of parts without creating unnecessary material wastage, does not require any complicated packaging and occupies a minimal amount of space in the packed state.

DISCLOSURE OF INVENTION

This object is achieved by an elongated, strip-like film bandage comprising a plastic film, which on its one side is coated with a skin-friendly adhesive, a protective layer detachably fixed to the adhesive coating, and a stiffening layer, which is detachably fixed to the plastic film on the opposite side to the adhesive coating, characterized in that the bandage is bellows-folded into a stack such that the bandage is divided into a number of parts stacked one on top of the other, and three such parts of the bandage, which are mutually adjacent, are connected to one another on two opposite sides of the stack. As a result of the concertinaing, fold notches (i.e., fold lines), illustrated as F and F' in FIGS. 1 and 3, respectively, are created in the stiffening layer, which means that it is easy for a user to place a folded-out part back into the folded stack. It is therefore not important that only the desired length of the part of the bandage which is to be cut off is unwound, which means that feed-out, cutting and re-creation of the stack of bellows-folded parts is easier to carry out and takes less time to perform than corresponding methods for a cut-off part of desired length of a bandage in roll form. Moreover, the handling of the stack is not complicated by folded parts of the film bandage at the end of its length, as in known traditional elongated, strip-like film bandages, which have a tendency to curl which increases with reducing radius of curvature. Furthermore, it is much easier to judge how many folded-together parts need to be unfolded to produce a certain desired length of the cut-off part than to judge how much a roll needs to be unwound to produce a desired length, which means that, in a bandage according to the invention, the likelihood of too many parts of the bellows-folded bandage being unfolded is relatively small. The stack of folded-together parts of the bandage is expediently stored in a rectangular or square box, which means that a plurality of such packagings can be stacked one upon the other and side by side without the creation of any dead space, unlike roll-shaped bandages in which dead spaces are created either in the packaging for the roll or when such rolls are stacked one upon the other and side by side.

In a preferred embodiment, a series of separate openings are formed in the stiffening layer and the distance between adjacent openings in the stiffening layer is equally large along the entire length of the bandage. Preferably, each opening in the stiffening layer extends between adjacent folds formed in the concertinaing of the bandage.

In a second embodiment, the stiffening layer, in each part in the stack of parts created by the concertinaing, has two or more openings. The distance between adjacent openings situated in successive folded parts of the bandage can be greater than the distance between adjacent openings situated in one such folded part.

In all embodiments, the stiffening layer can comprise a plurality of cuts, which extend from a longitudinal edge of the stiffening layer to the edge of an opening in this layer, and the stiffening layer, at a number of places along the length of the bandage, can extend transversely beyond the underlying plastic film, whereby a series of grip tabs are formed to facilitate removal of the stiffening layer.

BRIEF DESCRIPTION OF DRAWINGS

The invention will now be described with reference to the appended figures, of which.

MODE(S) FOR CARRYING OUT THE INVENTION

Figure 1:
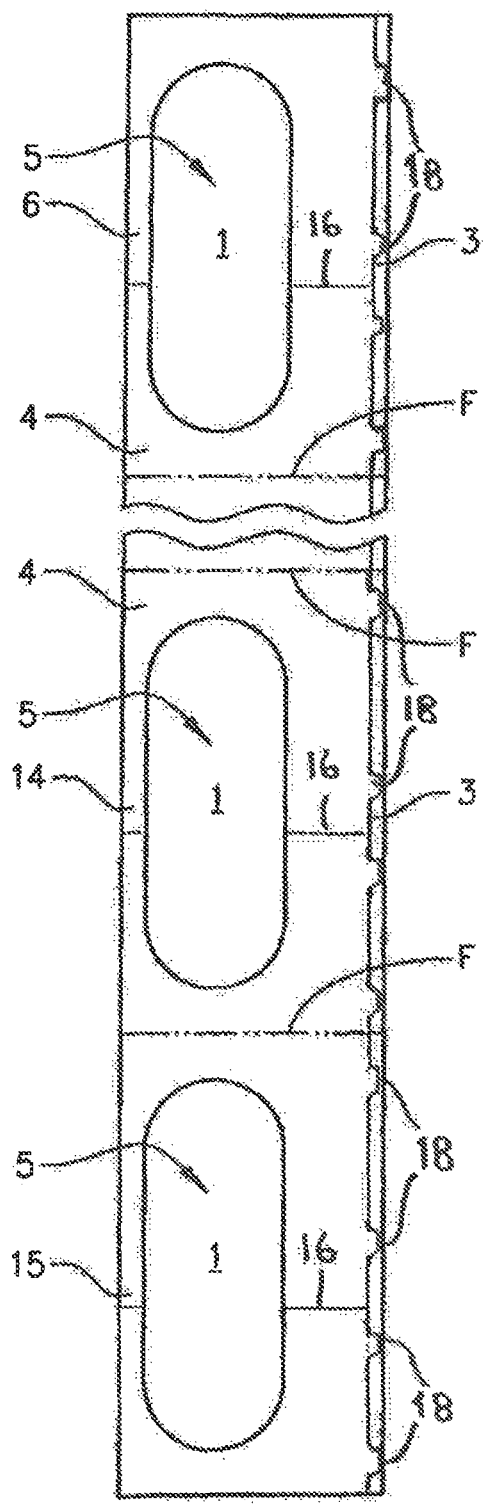
FIG. 1 shows in diagrammatic representation a plan view from above of an elongated, strip-like film bandage according to a first preferred embodiment of the invention.
Figure 2:
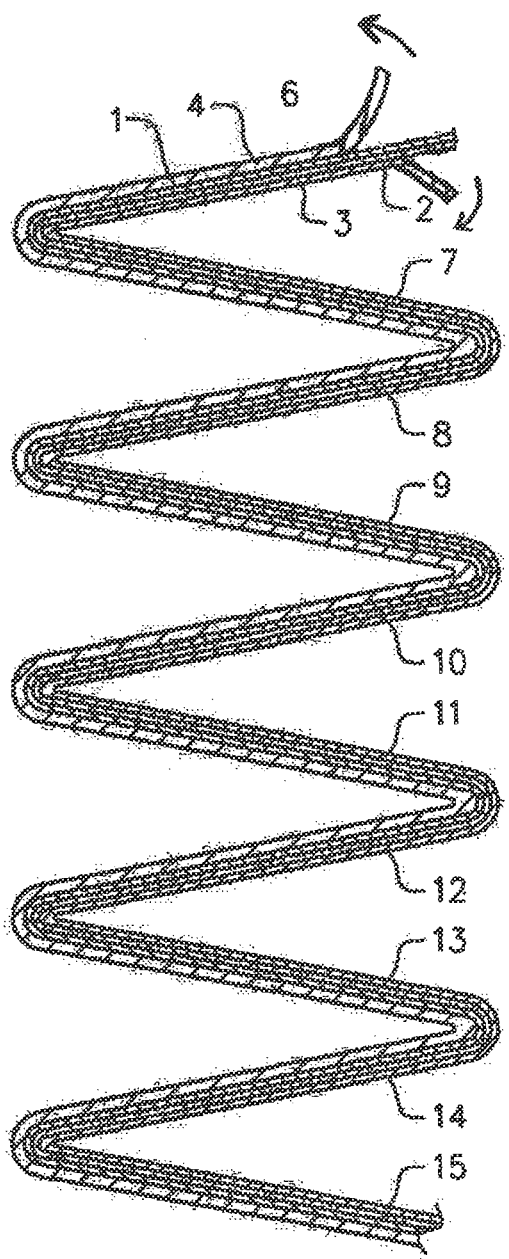
FIG. 2 shows in diagrammatic representation a side view of the bandage in FIG. 1 in the half-folded state.

A first preferred embodiment of an elongated, strip-like film bandage according to the invention is shown in diagrammatic representation in FIGS. 1 and 2 in a plan view from above and in a side view respectively. The film bandage is customarily made of a plastic film 1, which on its bottom side is coated with an adhesive layer 2 of skin-friendly adhesive, preferably a PSA (Pressure Sensitive Adhesive), usually polyacrylate, but other adhesives may also be used, such as SBR, silicones. The plastic film preferably consists of polyurethane film with a thickness of between 0.015 and 0.040 mm, but other breathable films can also be used, such as polyester-based films.

In order to protect the adhesive layer prior to use, a protective layer 3, a so-called release layer, is applied thereto. Since this layer has to be removed prior to use, without thereby damaging the properties of the adhesive layer, the protective layer 3 must have a weak adhesion to the adhesive. The material in the protective layer is therefore dependent on the properties of the adhesive. If the adhesive is constituted by a silicone adhesive, the protective layer can advantageously be constituted by a polyethylene film with a thickness of 0.05-0.20 mm. In other types of adhesive, for example acrylate glues, the protective layer can consist of so-called release paper of conventional configuration.

In order to facilitate application of the film bandage, a stiffening layer 4 is detachably fixed to the plastic film 1 on the top side thereof, i.e. on the side which has no adhesive layer 2. The stiffening layer is removed from the bandage directly after the bandage is applied and must therefore not be fixed too strongly to the plastic film 1. All the materials which are used as stiffening layers on film bandages can be used in a bandage according to the present invention, for example polyethylene film, paper or laminate of paper and polyethylene.

The elongated film bandage according to the invention has a longitudinal series of openings 5, which are equidistant from one another in the longitudinal direction. The plastic film 1 and the adhesive layer 2 are preferably transparent, which enables underlying wounds or skin to be viewed through these openings even if the stiffening layer is not made of transparent material.

In FIG. 1, the elongated film bandage is shown in the shape it has following its production. In FIG. 2, a side view is shown of the bandage in the half-folded state. As can be seen from this figure, the bandage is bellows-folded, so that a stack of folded parts 6-15, lying one upon the other, is created after the folding. A bandage of the type shown in the figures is intended to be used in such a way that the user himself decides how large a length of the elongated film bandage is required and cuts off the desired length from the elongated, strip-like bandage. In order to make it easier to judge how many folded parts are required for the intended use of the parts, the parts are preferably equal in size. In FIG. 1, the fold lines are indicated with the lines F and are placed at equal distances from each opening 5 in the stiffening layer. The distance between the fold lines F is expediently 5-15 cm and the distance between successive openings 5 is between 5 and 40 mm, preferably 20 mm.

The folded film bandage is designed to be placed in a lidded box so that, upon use, the upper end of the bandage is lifted up such that the desired number of parts are lifted out of the packaging, whereafter the bandage is cut off at the intended place. Another way of extracting the desired length of film bandage from the packaging is, instead of taking hold of the upper end of the bandage, to stick a finger into a fold situated a little way down in the folded stack and to then lift out of the packaging that part of the stack which is situated above the part so as to execute the cut with the desired length of bandage still in the folded state. By calculating the number of folds, it is easy to determine the length of the folded part of the stack which has to be removed, as well as in which fold the finger has to be inserted. The latter described method is particularly expedient if the cut-off length is large.

Figure 3:
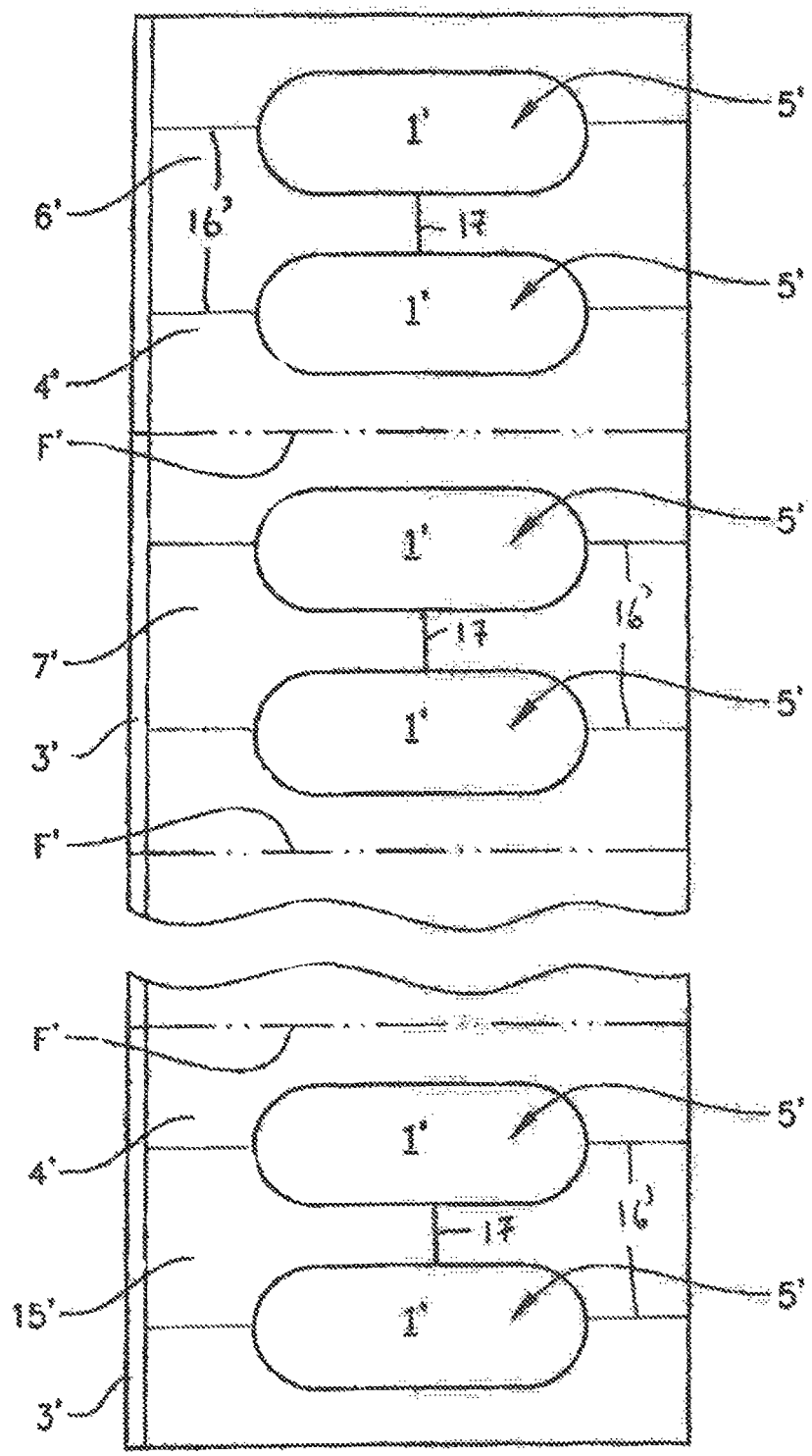
FIG. 3 shows in diagrammatic representation a plan view from above of an elongated, strip-like film bandage according to a second preferred embodiment.
Figure 4:
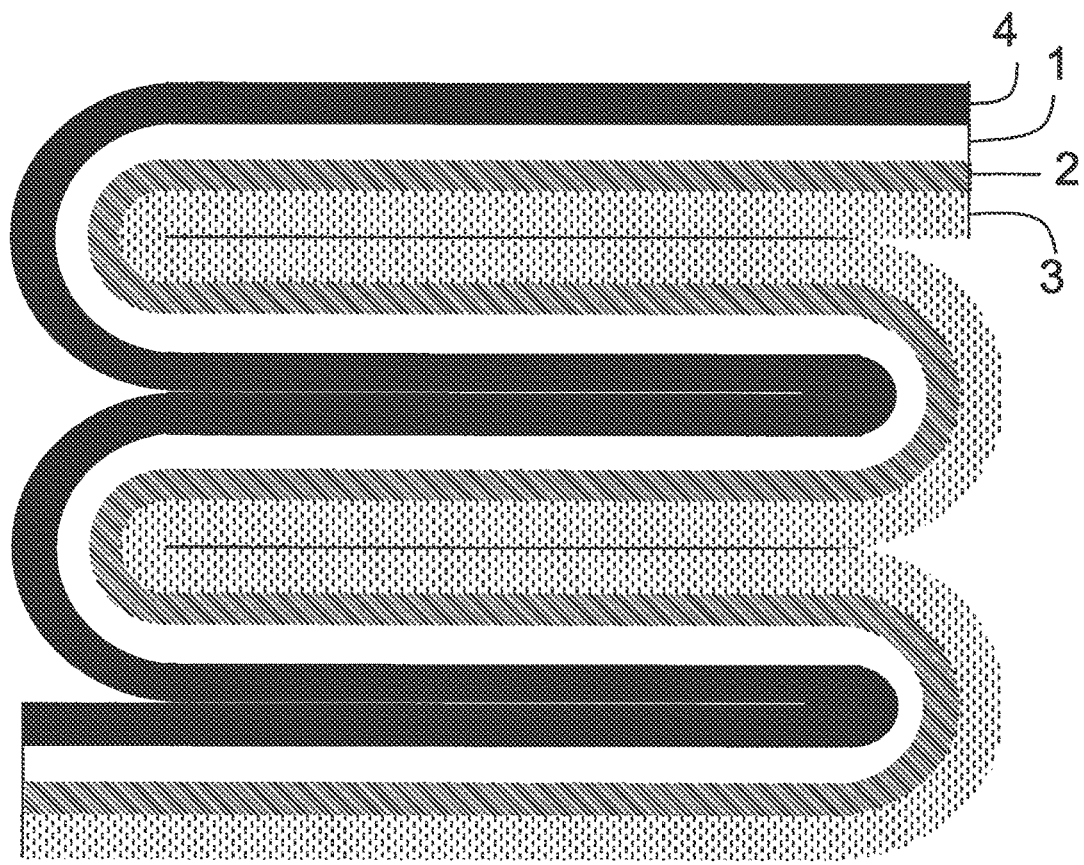
FIG. 4 illustrates a fully folded elongated, strip-like film bandage, in accordance with one embodiment.

When the film bandage is compressed from the half-folded state shown in FIG. 2 to the fully folded state shown in FIG. 4, fold notches (i.e., fold lines), illustrated as F and F' in FIGS. 1 and 3, respectively, are produced in the stiffening layer and the protective layer, which makes it very easy to return unfolded parts of the film bandage to the stack remaining in the packaging if too large a length of bandage has happened to be pulled or lifted out when extracting the length of bandage which has to be cut off.

In order to make the protective layer 3 easier to remove before the bandage is fixed to the skin, it extends on one side beyond the adhesive-coated film 1 so as to form a grip edge, as is shown in FIG. 1. It is also possible to make the stiffening layer likewise extend beyond the longitudinal edge of the adhesive-coated film in order to facilitate removal of the stiffening layer after the cut-off part of the bandage has been applied. Such grip edges can, of course, be disposed along both longitudinal edges of the adhesive coated film. Instead of making the entire protective layer or stiffening layer extend transversely beyond the adhesive-coated film, a series of grip tabs 18 can be disposed along one or both longitudinal edges of the film bandage.

In FIG. 3, a second embodiment of an elongated, strip-like film bandage is shown, which differs from the bandage in FIGS. 1 and 2 merely by the fact that, instead of an opening 5 in each folded part of the bandage, as in the first embodiment, the bandage according to the second embodiment has two openings 5' in each folded part. Those components in the second embodiment according to FIG. 3 which correspond to like components in the bandage according to FIGS. 1 and 2 have been given the same reference symbols with the addition of a prime sign. The bandage in FIG. 3 therefore comprises a series of pairs of openings 5', each pair of openings 5' in the series being equidistant from one another. The distance between the pairs of openings is greater than the distance between the openings in each pair of openings.

In order to facilitate removal of the stiffening layer, the stiffening layer can be cut through at a number of places along the length of the bandage. A series of first through-cuts 16 and second through-cuts 16' can extend from one or both longitudinal edges of the stiffening layer in towards an opening 5, 5' and up to the edge thereof. In addition, a series of third through-cuts 17 can also extend in the transverse direction between adjacent openings to allow parts of the stiffening layer to be successively removed during the application process. Such transverse through-cuts should not, however, extend into the folds of the bellows folded bandage, since there is then a risk of the stiffening layer then accidentally becoming detached from the plastic film.

The described embodiments can, of course, be modified within the scope of the invention. For example, more than two openings can be made in each folded part, the openings 5' in the pairs of openings could be orientated with their longitudinal extent in the longitudinal direction instead of the transverse direction as shown in FIG. 3, and the openings could have a different shape from that shown in the figures, for example rectangular, square, circular, etc. The invention shall therefore only be limited by the content of the appended patent claims.

The invention claimed is:

1. An elongated, strip-like film bandage, comprising:
a continuous plastic film,
a continuous skin-friendly adhesive coating on one side of the plastic film,
a continuous protective layer detachably fixed to the adhesive coating, and
a stiffening layer detachably fixed to the plastic film on a side opposite to the adhesive coating, wherein the bandage is bellows-folded into a stack, such that each of the plastic film, the skin-friendly adhesive coating, and the protective layer is bellows-folded to form a continuous bandage.

2. The elongated, strip-like film bandage of claim 1, in which a series of separate openings are formed in the stiffening layer.

3. The elongated, strip-like film bandage of claim 2, in which a distance between the separate openings in the stiffening layer is equally large along an entire length of the bandage.

4. The elongated, strip-like film bandage of claim 3, in which each of the separate openings in the stiffening layer extends between adjacent folds formed in a concertinaing of the bandage.

5. The elongated, strip-like film bandage of claim 2, wherein the stack comprises a plurality of connected parts, and wherein the stiffening layer, in each part in the stack created by a concertinaing, has two or more openings.

6. The elongated, strip-like film bandage of claim 5, wherein the stack comprises a plurality of connected parts, and wherein a distance between each of the separate openings situated in successive folded parts of the bandage is greater than a distance between separate openings situated in one such folded part.

7. The elongated, strip-like film bandage of claim 1, in which the stiffening layer comprises a plurality of cuts, which extend from a longitudinal edge of the stiffening layer to an edge of an opening in the stiffening layer.

8. The elongated, strip-like film bandage of claim 2, in which the stiffening layer comprises a plurality of cuts, which extend from a longitudinal edge of the stiffening layer to an edge of an opening in the stiffening layer.

9. The elongated, strip-like film bandage of claim 3, in which the stiffening layer comprises a plurality of cuts, which extend from a longitudinal edge of the stiffening layer to an edge of an opening in the stiffening layer.

10. The elongated, strip-like film bandage of claim 4, in which the stiffening layer comprises a plurality of cuts, which extend from a longitudinal edge of the stiffening layer to an edge of an opening in the stiffening layer.

11. The elongated, strip-like film bandage of claim 5, in which the stiffening layer comprises a plurality of cuts, which extend from a longitudinal edge of the stiffening layer to an edge of an opening in the stiffening layer.

12. The elongated, strip-like film bandage of claim 6, in which the stiffening layer comprises a plurality of cuts, which extend from a longitudinal edge of the stiffening layer to an edge of an opening in the stiffening layer.

* * * * *